United States Patent [19]

Hunt et al.

[11] Patent Number: 5,109,398
[45] Date of Patent: Apr. 28, 1992

[54] VERTICAL CORE FLOW TESTING APPARATUS AND METHOD WITH COMPUTED TOMOGRAPHY SCANNING

[75] Inventors: Patricia K. Hunt, Solon; Michael J. King, Cleveland Heights; Charles Blaha, Seven Hills, all of Ohio

[73] Assignee: BP America Inc., Cleveland, Ohio

[21] Appl. No.: 483,231

[22] Filed: Feb. 22, 1990

[51] Int. Cl.⁵ .............................................. H05G 1/00
[52] U.S. Cl. .................................... 378/208; 378/20; 378/207; 250/253
[58] Field of Search ............... 250/253, 254, 255, 256; 378/208, 4, 20, 25, 21, 68, 195, 67, 177, 207

[56] References Cited

U.S. PATENT DOCUMENTS 4,710,946  12/1987  Hinch et al. .................. 250/255
4,893,504  1/1990  O'Meara, Jr. et al. ............ 73/153

Primary Examiner—Janice A. Howell
Assistant Examiner—Don Wong
Attorney, Agent, or Firm—Renner, Otto, Boisselle & Sklar

[57] ABSTRACT

An apparatus and method for conducting and imaging vertical flow tests through a sample of porous material on-line in a CT scanner, characterized by a sample of porous material, such as a core sample, having a vertical axis and a transversely extending horizontal axis defining a scan plane to be imaged by the CT scanner. The sample is of uniform transverse width in the scan plane and has top and bottom end surfaces and opposite transverse side surfaces. The invention is further characterized by opposite filler bodies, of a material having an X-ray attenuation characteristic similar to the X-ray attenuation characteristic of the sample, juxtaposed against the side surfaces of the sample, respectively. The filler bodies have inner surface adjacent the sample and outer side surfaces that are round in the scan plane for forming with the sample a round shape for scanning in the scan plane. Also provided are top and bottom end pieces in fluid communication with the top and bottom surfaces, respectively. The end pieces include flow passages for passage of fluids into and out of the sample at the top and bottom end surfaces thereof. Provision is also made for securing together the sample, filler bodies and end pieces.

27 Claims, 2 Drawing Sheets

VERTICAL CORE FLOW TESTING APPARATUS AND METHOD WITH COMPUTED TOMOGRAPHY SCANNING

TECHNICAL FIELD OF THE INVENTION

The invention herein described relates generally to non-destructive analysis of mineral samples and, more particularly, to a new apparatus and method for conducting and imaging vertical core flow tests using computed tomography. A typical field for the application of this invention is in the sampling and testing of core samples from oil and gas wells. Although not limited to this use, the invention is hereafter described with respect to this use.

BACKGROUND OF THE INVENTION

In the production of minerals such as oil and gas, various laboratory procedures have been developed and used to determine lithological properties of a subterranean reservoir formation. These procedures include core flooding experiments wherein various fluids are caused to flow through a reservoir rock core sample.

Recently, computed tomography (CT) has been used to monitor core flooding experiments to aid in enhanced oil recovery and fluid mobility control. Such experiments may involve flushing a fluid through a core sample and monitoring the shape of the fluid fronts. By subtracting the images of the core samples before and after flooding, the shapes of the fluid front may be determined. The use of CT allows the interior of the core sample to be observed without disturbing the sample.

Core samples obtained by conventional coring techniques typically are three or four inches in diameter. Usually the axis of the core sample is aligned with the axis of the CT scanner and cross-sectional image slices perpendicular to the core axis are taken as the sample moves axially through the scanner.

Apparatus for positioning and moving a core sample through a CT scanner is shown and described by Vinegar et al in U.S. Pat. No. 4,583,242. The apparatus comprises a holding tube which is mounted on trolleys for axial movement through the CT scanner or, more particularly, computerized axial tomographic (CAT) scanner. The core sample is held by a sample holder concentrically within the holding tube and fluids can be injected at one end of the core sample and displaced fluids discharged from the opposite end for conducting core flooding experiments.

The above and similar apparatus set-ups are well suited to the performance of horizontal core flow tests since the axis of the CT scanner is oriented horizontally. However, some laboratory flow tests may require the fluids to flow vertically through the core sample (top to bottom or bottom to top) to more closely simulate processes occurring in petroleum reservoirs. This presents a problem when it is desired to carry out these tests on-line in a CT scanner so that the fluids can be imaged as they flow vertically through the core. Turning conventional horizontal core flow set-ups on end is undesirable for several reasons. The imaged cross-section of the core sample will be rectangular and this can cause false artifacts in the image. For best results the object being scanned should be circular or round. In addition, the cross-sectional area of the core sample will vary from slice-to-slice because the image will be taken along different chordal planes as the core sample is indexed through scanner in a direction perpendicular to its axis. Consequently, a need exists for an apparatus and method for conducting and imaging vertical core flow tests on-line in a horizontal axis CT scanner.

SUMMARY OF THE INVENTION

The present invention provides an apparatus and method for conducting and imaging vertical flow tests through a sample of porous material on-line in a CT scanner. The apparatus and method are characterized by a sample of porous material, such as a core sample, having a vertical axis and a transversely extending horizontal axis defining a scan plane to be imaged by the CT scanner. The sample is of uniform transverse width in the scan plane and has top and bottom end surfaces and opposite transverse side surfaces. The invention is further characterized by opposite filler bodies, of a material having an X-ray attenuation characteristic similar to the X-ray attenuation characteristic of the sample, juxtaposed against the side surfaces of the sample, respectively. The filler bodies have inner surfaces adjacent the sample and outer side surfaces that are round in the scan plane for forming with the sample a round shape for scanning in the scan plane. Also provided are top and bottom end pieces in fluid communication with the top and bottom surfaces, respectively. The end pieces include flow passages for passage of fluids into and out of the sample at the top and bottom end surfaces thereof. Provision is also made for securing together the sample, filler bodies and end pieces.

More particularly, the invention provides for on-line CT imaging of a sample set-up for vertical flow while eliminating image artifacts that otherwise may arise from the rectangular cross-sectional shape of the sample in the scan plane. Typically, the sample has planar top and bottom surfaces and is of uniform cross-sectional area going from top to bottom. Such a sample may be rendered more conducive to CT scanning by positioning the filler bodies at opposite transverse sides of the sample to impart thereto a round or more round shape for imaging. Similarly, additional bodies may be disposed at opposite transverse sides of the end pieces to form a generally round outer layer. These additional bodies are of a material that has an X-ray attenuation coefficient similar to the X-ray attenuation coefficient of the end pieces. Also provided is an inner casing enclosing the sides of the sample and an outer jacket which holds the sample and filler bodies together.

According to another aspect of the invention, an apparatus for imaging an unround rock sample in a CT scanner or other noninvasive scanner comprises a rock sample having a vertical axis and a transversely extending horizontal axis defining a scan plane to be imaged by the CT scanner. The rock sample has an unround cross-sectional shape in the scan plane that may be contained within a round cross-sectional shape, and the unround and round cross-sectional shapes define therebetween at least one segment area in said scan plane. One or more filler pieces of material having an X-ray attenuation characteristic similar to the X-ray attenuation characteristic of the rock sample are provided for filling the segment area in the scan plane, and provision is made for holding the filler pieces in fixed position relative to the rock sample.

According to a further aspect of the invention, a method for conducting and imaging vertical flow tests through a sample of porous material in a CT scanner comprising the steps of (a) a sample of porous material having a vertical axis and a transversely extending horizontal axis defining a scan plane to be imaged by the CT scanner, the sample being of uniform transverse width in the scan plane and having top and bottom end surfaces and opposite transverse side surfaces; (b) assembling opposite filler bodies, of a material having an X-ray attenuation characteristic similar to the X-ray attenuation characteristic of said sample, against said side surfaces, respectively, with the filler bodies having inner surfaces adjacent the sample and outer side surfaces that are rounded in the scan plane for forming with the sample a composite sample having a substantially round shape for scanning in the scan plane; (c) assembling top and bottom end pieces in fluid communication with the top and bottom surfaces of the sample, respectively, the end pieces including flow passages for passage of fluids into and out of said sample at the top and bottom end surfaces thereof; (d) positioning and orienting the sample, filler bodies and end pieces in a CT scanner with the scan plane disposed perpendicular to the axis of the scanner; (e) supplying fluid to one of the end pieces and discharging displaced fluid through the other end piece to effect vertical fluid flow through the sample; and (f) scanning the sample in the scanner to obtain image data for at least one vertical transverse slice through the sample while maintaining the vertical orientation of the sample in the scanner.

The foregoing and other features of the invention are hereinafter fully described and particularly pointed out in the claims, the following description and annexed drawings setting forth in detail an illustrative embodiment of the invention, this being indicative, however, of but one of the various ways in which the principles of the invention may be employed.

DETAILED DESCRIPTION OF THE INVENTION

Figure 1:
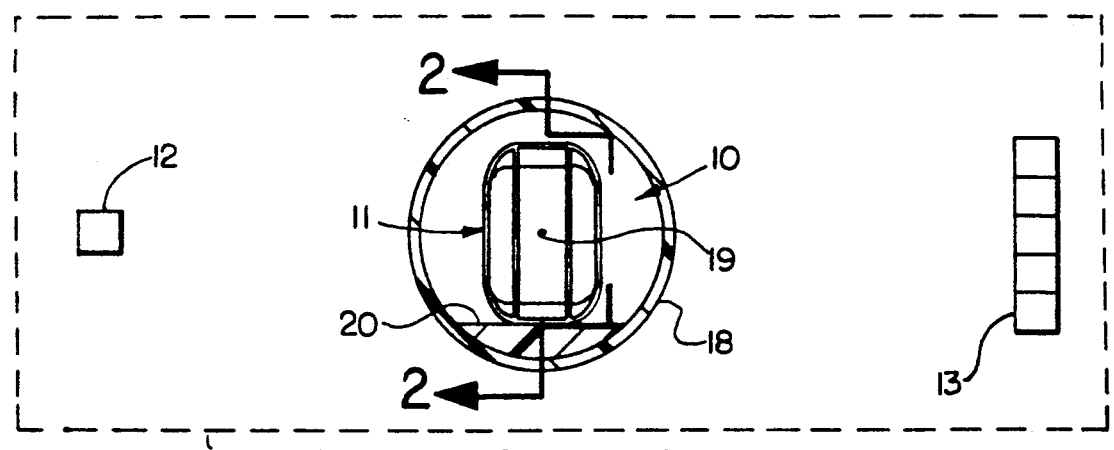
FIG. 1 is a sectional view through a CT scanning system showing a vertical core flow testing apparatus according to the invention.
Figure 2:
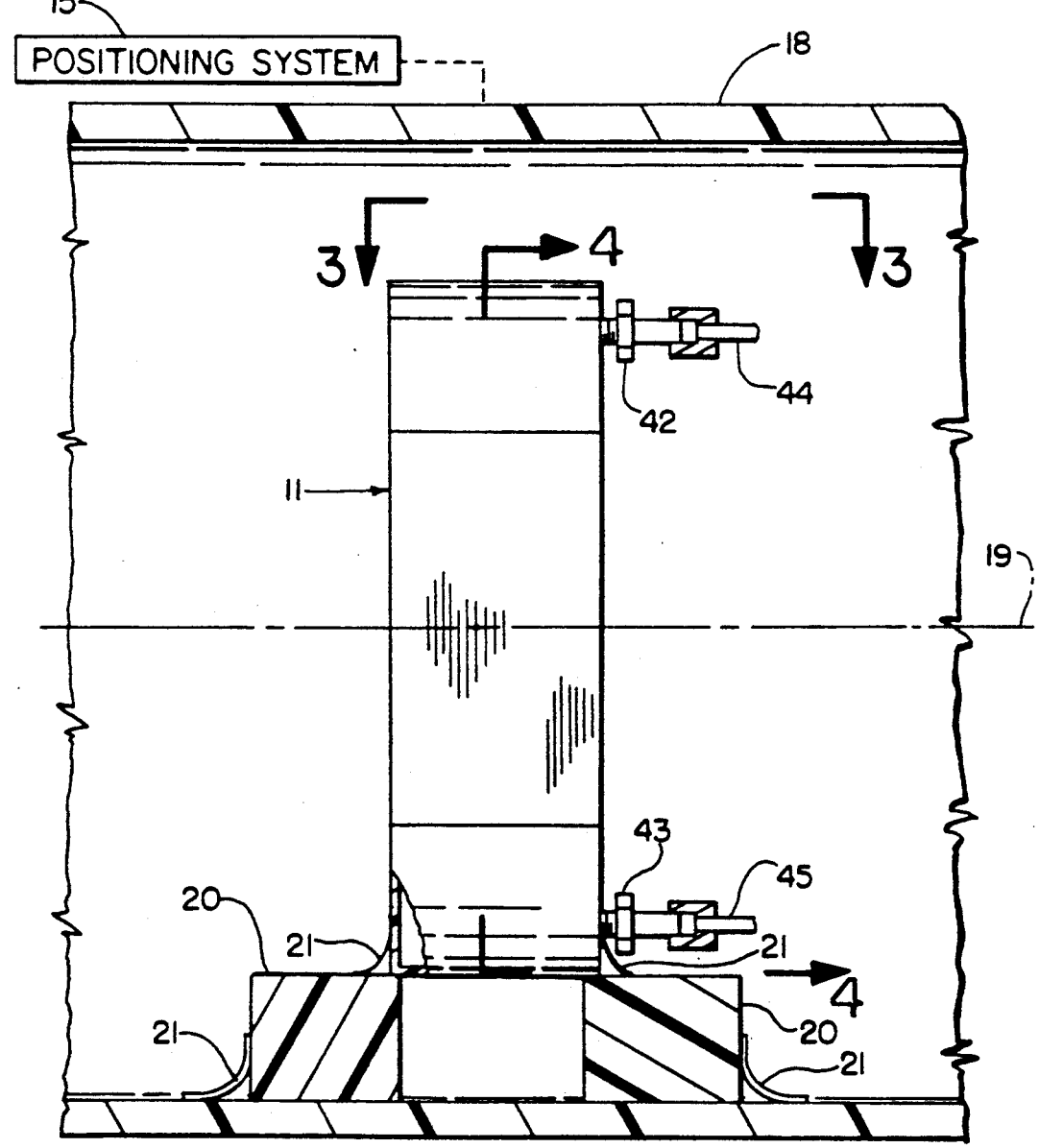
FIG. 2 is a sectional view taken along the line 2—2 of FIG. 1.

Referring now in detail to the drawings and initially to FIGS. 1 and 2, a vertical flow test apparatus according to the invention is indicated generally at 10. The apparatus 10 includes a sample assembly 11 which is shown in relation to the X-ray source 12 and detector or detectors 13 of a conventional CAT scanner diagrammatically represented by broken line box 14. The CAT scanner 14 may be of the type described by Vinegar et al in U.S. Pat. No. 4,583,242. This patent is hereby incorporated herein by reference for its description of a suitable CAT scanner and sample positioning system that may be used in practicing the present invention. In FIG. 2 the sample positioning system, like that shown and described in U.S. Pat. No. 4,583,242, is diagrammatically represented by box 15. Operation of the scanning system for core analysis may be facilitated by software available from the Shell Oil Company, Houston, Tex.

The sample positioning system 15, as disclosed in U.S. Pat. No. 4,583,242, includes a holding tube 18 in which the sample assembly 11 is carried for translation through the CAT scanner 14 in a direction parallel to the axis 19 of the holding tube 18. The axis 19 of the holding tube is coaxial with the axis of the scanner 14.

The sample assembly 11 is supported in the holding tube by a pair of axially spaced apart support blocks 20. The support blocks have arcuate bottom surfaces for stable resting on the interior bottom surface of the holding tube and flat top surfaces on which the sample assembly is supported and secured by tape 21. Tape 21 also may be used to attach the support blocks 20 to the interior surface of the holding tube 18.

The support blocks 20 are axially spaced apart and axially offset in opposite directions from the sample assembly 11 except for a slight overlap at the axially outer bottom edges of the sample assembly. Consequently, the sample assembly 11 may be imaged over substantially its entire axial thickness without interference by the support blocks 20.

Figure 3:
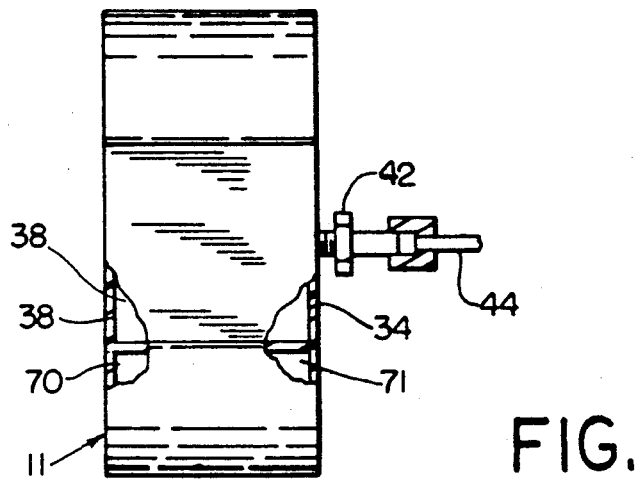
FIG. 3 is a plan view of the apparatus looking from the line 3—3 of FIG. 2.

Although not shown, the holding tube 18 may be provided with a removable window to facilitate the positioning of the sample assembly 11 in the holding tube, as is known in the art. The holding tube preferably is made of a material that is optically transparent and mechanically strong and which has a low X-ray absorption, such as plexiglass. The support blocks 20 also preferably are made of a material, preferably plastic, that has a low X-ray absorption., With additional reference to FIGS. 3 and 4, the sample assembly 11 has a vertical axis 24 and a transverse horizontal axis 25. The sample assembly is positioned in the holding tube 18 such that the intersection point 26 of the two axes 24 and 25 is centered in the holding tube and the plane defined by the two axes is oriented perpendicular to the tube axis 19. Consequently, a CT scan slice through the assembly will correspond to a vertical-transverse slice through the sample assembly.

The sample assembly 11 comprises a sample 28 of a porous material, such as a core sample of a subterranean reservoir rock formation, to be examined in accordance with the present invention. The sample 28 preferably is centered in the assembly 11 such that it has a vertical axis and a transversely extending horizontal axis coinciding with the axes 24 and 25 of the sample assembly, respectively. The sample is of uniform transverse width and has top and bottom end surfaces 29 and 30 and opposite transverse side surfaces 31 and 32. The transverse side surfaces 31 and 32 are parallel to one another whereby the sample has a uniform transverse width. In the illustrated embodiment, the sample is square in horizontal cross-section and has four rectangular side faces. The side faces or surfaces 31 and 32 are opposite one another along the transverse horizontal axis 25 and the other two opposite side faces or surfaces 33 and 34 are opposite one another along the holding tube or scanner axis 19. As is desired for flow tests, the sample is of uniform cross-sectional area going from top to bottom.

The sample assembly 11 further comprises top and bottom fluid distribution end pieces 38 and 39. In the illustrated embodiment, the fluid distribution end pieces are essentially identical although oppositely oriented at opposite ends of the sample 28. Each end piece 38, 39 has an inlet/outlet port 40, 41 in which a fitting 42, 43 in installed. Attached to the fitting is a fluid line 44, 45 through which fluid may be supplied to the sample or displaced fluid removed from the sample, depending on whether upward or downward flow is desired. As seen in FIG. 2, the fitting extends from an axial side face of the end piece so that it will not show up in the CT scan images.

Each end piece 38, 39 has an inner planar surface 48, 49 which is butted against the corresponding planar end surface 29, 30 of the sample 28. The inner surface 48, 49 has formed therein an array or network of distribution passages 50, 51 which communicate with the inlet/outlet port 40, 41 via a narrow passage 52, 53. The network pattern may be varied as needed to obtain a flow pattern at the corresponding end face of the sample that is desired for a given flow test. Fluid supplied to the port 40 in the end piece 38, for example, will be distributed across the top surface of the sample 28 for flow downwardly through the sample 28. The resulting fluid front will displace fluid already residing in the sample and displaced fluid will flow into the network of passages 51 in the bottom end piece 39 for discharge through port 41.

The end pieces 38 and 39 in the illustrated embodiment are of the same cross-sectional shape and size as the end surfaces 29 and 30. Accordingly, the end pieces 38, 39 completely close the end faces apart from the fluid path established by the passages in the end pieces. As for the side surfaces 31–34 of the sample 28, they are enclosed by a layer 56 of epoxy or other suitable encasing material. The epoxy layer forms a sample casing which closely surrounds the sample and the adjacent end pieces to provide an encapsulated flow system. The epoxy layer or casing 56 also serves to securely hold the end pieces to the end faces of the sample. Other casing materials may be used if desired, such as a shrink-wrap plastic sleeve. The casing material preferably is a relatively low X-ray attenuation material such as plastic or epoxy.

Figure 4:
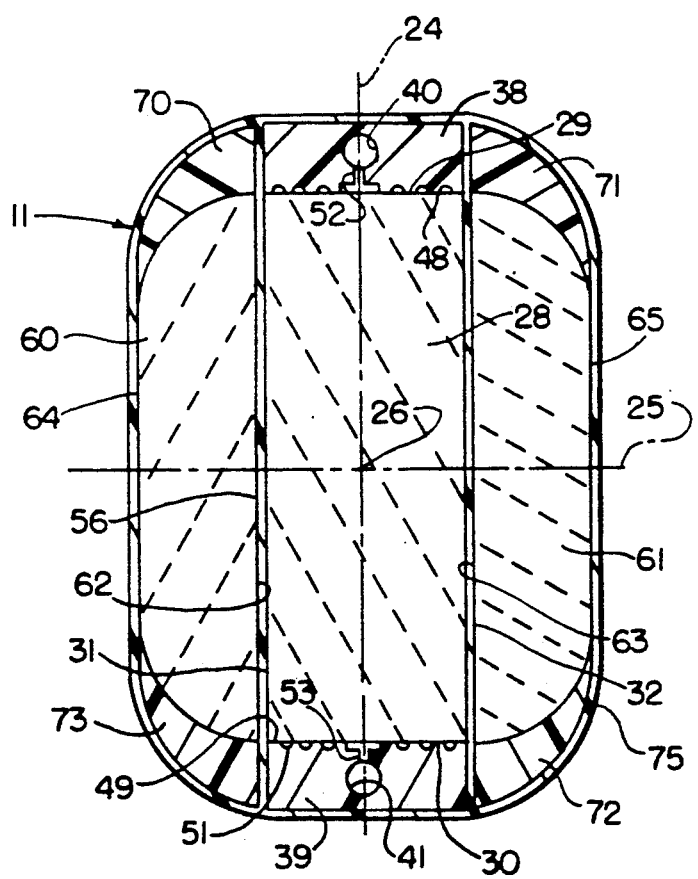
FIG. 4 is a sectional view taken along the line 4—4 of FIG. 2.

As seen in FIG. 4, the encapsulated flow system, comprising the sample 28 and end pieces 38 and 39, has a transverse cross-sectional shape that is rectangular. This is problematic in that CT image artifacts commonly occur when the object being scanned has an irregular shape or sharp corners. Occurrence of these problematic CT image artifacts may be prevented if the scanning X-rays see a rounded equidimensional shape.

To avoid CT image artifact problems, the sample assembly 11 further comprises filler bodies 60 and 61 of a material having an X-ray attenuation similar to that of the sample, such as more reservoir rock in the case of a reservoir core sample. The filler bodies are held in juxtaposition with respective side surfaces 31 and 32 of the sample 28 More particularly, the X-ray attenuation of the filler bodies should be equal to the X-ray attenuation of the sample +/−40%, preferably +/−20%, more preferably +/−10% and still more preferably +/−5%. The filler bodies 60 and 61 have flat transversely inner surfaces 62 and 63 butted against the walls of the casing 56 covering the sample side surfaces 31 and 32, respectively, and transversely outer side surfaces 64 and 65 which are rounded.

The inner surfaces 62 and 63 of the filler bodies 60 and 61 correspond in shape and size to the adjacent side surfaces 31 and 32 of the sample 28, and the outer side surfaces 64 and 65 of the filler bodies at their top/ and bottom edges tangentially meet the end surfaces 29 and 30 of the sample 28 to provide a smooth transition between the sample and filler bodies. Together the filler bodies and sample present in transverse cross-section an overall rounded or elliptical shape for CT imaging. If desired, the overall shape may more closely approximate a circular shape, however the illustrated shape has been found to enable collection of quality CT image data while a vertical flow test is being conducted in the gantry of the scanner.

In the illustrated embodiment the filler bodies and sample, herein collectively referred to as a composite sample, have a rectangular shape with well rounded corners. The minimum radius of the corner surfaces should be no less than one-fifth and more preferably no less than one-fourth the width of the composite sample along the minor axis thereof which corresponds to axis 25 in FIG. 4. Additionally, the width of the composite sample along the minor axis should be no less than one-half and preferably no less than three quarters the width of the composite sample along the major axis. The illustrated shape also may be viewed as elliptical with flattened surface portions at the poles. The flattened portions of the side surfaces 64 and 65 may be rounded if desired, but usually the end surfaces 29 and 30 will be substantially flat or planar for convenience and/or establishment of a planar fluid front.

As above indicated, the filler bodies 60 and 61 are of a material having an X-ray attenuation similar to that of the sample. Each filler body 60, 61 may be unitary or composed of several pieces assembled to provide the illustrated shaped body. The filler bodies are isolated from the sample 28 by the walls of the casing 56 so that fluid flows only through the sample and not through the filler bodies.

The sample assembly 11 also preferably includes corner bodies 70–73 having an X-ray attenuation similar to the X-ray attenuation of the end pieces to form a rounded continuation of the top and bottom end pieces 38 and 39. As seen in FIG. 4, each corner body at its transversely inner end corresponds in vertical thickness to the vertical thickness of the adjacent side of the corresponding end piece. Moving outwardly, each corner body is curved and tapered in thickness to impart a rounded corner to the overall shape of the sample assembly. Ideally, these corner bodies are made of the same material as the end pieces such as plastic. The X-ray attenuation of the corner bodies should be equal to the X-ray attenuation of the end pieces +/−40%, preferably +/−20%, more preferably +/−10% and still more preferably +/−5%.

The filler bodies 60 and 61 and corner bodies 70–73 are held together and to the sample 28 by a layer 75 of epoxy or other suitable material. The epoxy layer 75 forms an outer jacket which closely surrounds and encapsulates the sample assembly. Preferably the epoxy layer or jacket walls are of uniform thickness as are the walls of the inner casing 56. As seen in FIG. 2, the sample assembly 11 overlaps each support block 20 by the thickness of the jacket wall.

The addition of the outer jacket and corner bodies of low attenuation material should not introduce any sharp corners and preferably the overall shape of the sample assembly should satisfy the above set forth criteria respecting the roundness of the composite sample. For example, the minimum radius at rounded corner surfaces should not be less than one-fifth the width of the sample assembly (including the outer jacket) along the minor axis. In addition, the sample assembly should be symmetrical with respect to both the major and minor axes which define a plane parallel to the scanning plane of the CT scanner. In the illustrated embodiment the filler and corner bodies have the same thickness as the sample.

The sample assembly 11 may be housed within a pressure cell for subjecting the sample assembly and more particularly the sample 28 to varying pressure conditions. The pressure cell may include an aluminum containment barrel which assists in eliminating "cupping" artifacts which arise from the "beam hardening" phenomenon common in CT. Procedures for eliminating cupping affects are disclosed in Hunt et al "Calibrations for Analyzing Industrial Samples on Medical CT Scanners", Review of Progress in Quantitative Destructive Evaluation, Vol. 8A (Plenum Publishing Corporation 1989). The sample assembly also may be subjected to varying temperature conditions. The selection of the casing material and jacket material should be made with consideration being given to the pressures and temperatures to be established during flow testing of the sample.

The sample to be tested, for example, may be obtained from a core taken from a borehole in a reservoir rock formation. A 4 inch core can yield a sample that is 3 inch square in cross-section perpendicular to the core axis. The height of the sample normally will be dictated by the maximum scan circle diameter of the CT scanner. An exemplary core sample is 3 inch square in cross-section and 4 inches in height. The sample dimensions will of course vary from situation to situation. For example, a 4 inch core which has been invaded by drilling mud may yield a much smaller cross-section of uninvaded rock such as, for example, a 1½ inch by 1½ inch cross-section sample having a height of 4 inches, this corresponding to the embodiment illustrated in the drawings.

With the sample assembly 11 installed as shown in FIGS. 1 and 2, conventional fluid flow tests may be performed on the sample to obtain information regarding lithological properties of the sample, such as porosity or permeability. During performance of the flow test, the sample is scanned in the scanner by X-rays to obtain CT image data for one or more vertical-transverse slices through the sample. The image data may then be analyzed to determine lithological properties of the sample, using imaging and analysis techniques known in the art. This "on-line" scanning allows the sample assembly to be maintained during flow testing at the same location in the holding tube whereby specific scan planes may be relocated multiple times during a flow test.

Although the invention has been shown and described with respect to a preferred embodiment, it is obvious that equivalent alterations and modifications will occur to others skilled in the art upon the reading and understanding of this specification. The present invention includes all such equivalent alterations and modifications, and is limited only by the scope of the following claims.

What is claimed is:

1. An apparatus for conducting and imaging vertical flow tests through a sample of porous material in a CT scanner, comprising
   a sample of porous material having a vertical axis and a transversely extending horizontal axis defining a scan plane to be imaged by the CT scanner, said sample being of uniform transverse width in said scan plan and having top and bottom end surfaces and opposite transverse side surfaces;
   opposite filler bodies, of a material having an X-ray attenuation characteristic similar to the X-ray attenuation characteristic of said sample, juxtaposed against said transverse side surfaces. respectively, said filler bodies having inner surfaces adjacent said sample and outer side surfaces that are rounded in said scan plane for forming with said sample a composite sample having a substantially round shape for scanning in said scan plane, and each filler body being unitary or composed of several pieces assembled together;
   top and bottom end pieces in fluid communication with said top and bottom end surfaces, respectively, said end pieces including flow passage means for passage of fluids into and out of said sample at the top and bottom end surfaces thereof; and
   means for securing together said sample, filler bodies and end pieces.

2. An apparatus as set forth in claim 1, comprising means for encasing said sample between said end pieces.

3. An apparatus as set forth in claim 2, wherein said means for encasing includes a layer of encapsulating material interposed between said sample and filler bodies.

4. An apparatus as set forth in claim 3, wherein said encapsulating material has an X-ray attenuation characteristic that is low in relation to the X-ray attenuation characteristics of said sample and filler bodies.

5. An apparatus as set forth in claim 1, wherein said means for securing comprises an outer jacket surrounding said sample, filler bodies and end pieces.

6. An apparatus as set forth in claim 5, wherein said outer jacket is formed by a layer of epoxy material.

7. An apparatus as set forth in claim comprising curved corner bodies, of a material having an X-ray attenuation characteristic similar to the X-ray attenuation characteristic of said end pieces, juxtaposed against transverse side surfaces of said end pieces and extending at least part way over the rounded outer side surfaces of said filler bodies.

8. An apparatus as set forth in claim 7, wherein said end pieces and corner bodies have an X-ray attenuation characteristic that is low in relation to the X-ray attenuation characteristic of said sample and filler bodies.

9. An apparatus as set forth in claim 1, wherein said sample is a core sample taken from a subterranean reservoir.

10. An apparatus as set forth in claim 9, wherein said filler bodies are composed of rock.

11. An apparatus as set forth in claim 1, where in said sample is of uniform transverse cross-sectional area from top to bottom.

12. An apparatus as set forth in claim 1, wherein said top and bottom end surfaces are planar.

13. An apparatus for imaging an unround rock sample in a CT scanner or other noninvasive scanner, comprising
   a rock sample having a vertical axis and a transversely extending horizontal axis defining a scan plane to be imaged by the CT scanner, said rock sample having top and bottom end surfaces and an unround cross-sectional shape in said scan plane that may be contained within a round cross-sectional shape, said unround and round cross-sectional shape defining therebetween at least one segment area in said scan plane;
   top and bottom end pieces in fluid communication with said top and bottom end surfaces, respectively, said end pieces including fluid flow passage means for passage of fluids into and out of said sample at the top and bottom surfaces thereof;

filler material having an X-ray attenuation characteristic similar to the X-ray attenuation characteristic of said rock sample for filling said at least one segment area in said plane, said filler material having a rounded outer side terminating at upper and lower ends thereof at said top and bottom end pieces, respectively, such that said filler material does not substantially overlap said end pieces; and means for holding said filler material in fixed position relative to said rock sample.

14. A method for conducting and imaging vertical flow tests through a sample of porous material in a CT scanner, comprising the steps of obtaining a sample of porous material having a vertical axis and a transversely extending horizontal axis defining a scan plane to be imaged by the CT scanner, the sample being of uniform transverse width in the scan plan and having top and bottom end surfaces and opposite transverse side surfaces;

assembling opposite filler bodies, of a material having an X-ray attenuation characteristic similar to the X-ray attenuation characteristic of said sample, against said transverse side surfaces, respectively, with the filler bodies having inner surfaces adjacent the sample and outer side surfaces that are rounded in the scan plane for forming with the sample a composite sample having a substantially round shape for scanning in the scan plane, and each filler body being unitary or composed of several pieces assembled together;

assembling top and bottom end pieces in fluid communication with the top and bottom end surfaces of the sample, respectively, the end pieces including flow passages for passage of fluids into and out of said sample at the top and bottom end surfaces thereof;

positioning and orienting the sample, filler bodies and end pieces in a CT scanner with the scan plane disposed perpendicular to the axis of the scanner;

supplying fluid to one of the end pieces and discharging displaced fluid through the other end piece to effect vertical fluid flow through the sample; and scanning the sample in the scanner to obtain image data for at least one vertical-transverse slice through the sample while maintaining the vertical orientation of the sample in the scanner.

15. A method as set forth in claim 14, comprising the step of encasing the sample between the end pieces with a layer of encapsulating material.

16. A method as set forth in claim 15, wherein said encasing step includes using an encapsulating material having an X-ray attenuation characteristic that is low in relation to the X-ray attenuation characteristics of the sample and filler bodies.

17. A method as set forth in claim 14, wherein said assembling steps include securing together the sample, filler bodies and end pieces by surrounding the sample, filler bodies and end pieces with an outer jacket.

18. A method as set forth in claim 17, wherein the outer jacket is formed by a layer of epoxy material.

19. A method as set forth in claim 14, wherein said obtaining step includes taking the sample from a subterranean reservoir.

20. An apparatus as set forth in claim 1, wherein said transverse side surfaces are parallel.

21. An apparatus as set forth in claim 20, wherein said transverse side surfaces are generally planar.

22. An apparatus as set forth in claim 13, wherein said sample has opposite transverse side surfaces, and said filler material includes opposite filler bodies juxtaposed against said transverse side surfaces, said filler bodies having inner surfaces adjacent said sample and outer side surfaces that are rounded in said scan plane for forming with said sample a composite sample having a substantially round shape for scanning in said scan plan.

23. An apparatus as set forth in claim 13, including means extending from said end pieces at least part way around said filler material to form a continuation of said end pieces, said means to form having an X-ray attenuation characteristic similar to the X-ray attenuation characteristic of said end pieces.

24. An apparatus as set forth in claim 13, wherein said sample has generally planar and parallel side surfaces.

25. A method for conducting and imaging a vertical flow test through a sample of porous material in a CT scanner, comprising the steps of:

obtaining a sample of porous material having a vertical axis and a transversely extending horizontal axis defining a scan plane to be imaged by the CT scanner, the sample having top and bottom end surfaces and an unround cross-sectional shape in the scan plane that may be contained within a round cross-sectional shape, the unround and round cross-sectional shapes defining therebetween at least one segment area in the scan plane;

assembling top and bottom end pieces in fluid communication with the top and bottom end surfaces of the sample, respectively, the end pieces including flow passages for passage of fluids into and out of the sample at the top and bottom end surfaces thereof;

filling said at least one segment area in said plane with filler material having an X-ray attenuation characteristic similar to the X-ray attenuation characteristic of the sample, the filler material having a rounded outer side terminating at upper and lower ends thereof at the top and bottom end pieces, respectively, such that the filler material does not substantially overlap the end pieces;

positioning and orienting the sample filler material and end pieces in a CT scanner with the scan plane disposed perpendicular to the axis of the scanner;

supplying fluid to one of the end pieces and discharging displaced fluid through the other end piece to effect vertical fluid flow through the sample; and scanning the sample in the scanner to obtain image data for at least one vertical-transverse slice through the sample while maintaining the vertical orientation of the sample in the scanner.

26. A method as set forth in claim 25, including the step of forming continuations of the end pieces which extend at least part way around the filler material and which have an X-ray attenuation characteristic similar to the X-ray attenuation characteristic of the end pieces.

27. A method as set forth in claim 25, wherein the obtaining step includes providing a sample having generally planar and parallel side surfaces, and said filling step includes assembling opposite filler bodies, of a material having an X-ray attenuation characteristic similar to the X-ray attenuation characteristic of the sample, against the transverse side surfaces, respectively, with the filler bodies having inner surfaces adjacent the sample and outer side surfaces that are rounded in the scan plane for forming with the sample a composite sample having a substantially round shape for scanning in the scan plane.

* * * * *

UNITED STATES PATENT AND TRADEMARK OFFICE
CERTIFICATE OF CORRECTION

PATENT NO. : 5,109,398

DATED : April 28, 1992

INVENTOR(S) : Patricia K. Hunt et al.

It is certified that error appears in the above-identified patent and that said Letters Patent is hereby corrected as shown below:

Column 8:

In claim 7 at line 1, after "claim" there should be inserted --1--.

In claim 11 at line 1, "where in" should read --wherein--.

Signed and Sealed this

Seventeenth Day of August, 1993

Attest:

BRUCE LEHMAN

Attesting Officer

Commissioner of Patents and Trademarks